(12) United States Patent
Tsukuda et al.

(10) Patent No.: US 9,927,400 B2
(45) Date of Patent: Mar. 27, 2018

(54) FIELD ASYMMETRIC ION MOBILITY SPECTROMETER AND METHOD FOR SEPARATING MIXTURE USING THE SAME

(71) Applicant: Panasonic Intellectual Property Management Co., Ltd., Osaka (JP)

(72) Inventors: Masahiko Tsukuda, Osaka (JP); Tomohiro Ota, Hyogo (JP); Takeshi Yamamoto, Osaka (JP); Norihito Tsukahara, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/350,155

(22) Filed: Nov. 14, 2016

(65) Prior Publication Data

US 2017/0343510 A1    Nov. 30, 2017

(30) Foreign Application Priority Data

May 24, 2016   (JP) .................................. 2016-103183

(51) Int. Cl.
*H01J 49/26*      (2006.01)
*G01N 27/62*      (2006.01)
(Continued)

(52) U.S. Cl.
CPC ........ *G01N 27/622* (2013.01); *H01J 49/0031* (2013.01); *H01J 49/0422* (2013.01); *H01J 49/06* (2013.01)

(58) Field of Classification Search
CPC ................ G01N 27/622; H01J 49/0031; H01J 49/0422; H01J 49/02; H01J 49/06; H01J 49/061; H01J 49/062
(Continued)

(56) References Cited

U.S. PATENT DOCUMENTS 7,227,134 B2   6/2007   Miller et al.
8,319,177 B2   11/2012   Boyle et al.
(Continued)

FOREIGN PATENT DOCUMENTS

JP     2003-505846     2/2003
JP     2008-508693     3/2008

OTHER PUBLICATIONS

The Extended European Search Report dated Apr. 25, 2017 for the related European Patent Application No. 16198211.1.

*Primary Examiner* — Nicole Ippolito
(74) *Attorney, Agent, or Firm* — McDermott Will & Emery LLP

(57) ABSTRACT

The present invention provides a field asymmetric ion mobility spectrometer for selectively separating at least one kind of material from a mixture containing two or more kinds of materials. A filter included in the spectrometry comprises first—four plate-like electrodes each having a principal plane parallel to a direction from an ionizer toward a filter. The second plate-like electrode is located between the first plate-like electrode and the third plate-like electrode. The third plate-like electrode is located between the second plate-like electrode and the fourth plate-like electrode. The third and fourth plate-like electrodes are electrically connected to the first and second plate-like electrodes, respectively. An interspace is formed between two adjacent plate-like electrodes. The present invention provides a field asymmetric ion mobility spectrometer having high separation ability.

18 Claims, 9 Drawing Sheets

(51) Int. Cl.
*H01J 49/06* (2006.01)
*H01J 49/04* (2006.01)
*H01J 49/00* (2006.01)

(58) Field of Classification Search
USPC .................................. 250/281, 282, 283, 290
See application file for complete search history.

(56) References Cited

U.S. PATENT DOCUMENTS

| | | |
|---|---|---|
| 2008/0017790 A1 | 1/2008 | Boyle et al. |
| 2009/0173880 A1 | 7/2009 | Bateman et al. |
| 2009/0189064 A1* | 7/2009 | Miller .................. G01N 27/624 |
| | | 250/282 |
| 2011/0266432 A1 | 11/2011 | Ugarov |
| 2015/0060655 A1* | 3/2015 | Garside ................. H01J 49/065 |
| | | 250/281 |
| 2016/0181080 A1* | 6/2016 | Williams .............. H01J 49/063 |
| | | 250/292 |

* cited by examiner

FIELD ASYMMETRIC ION MOBILITY SPECTROMETER AND METHOD FOR SEPARATING MIXTURE USING THE SAME

BACKGROUND

1. Technical Field

The present invention relates to a field asymmetric ion mobility spectrometer and a method for separating a mixture using the same.

2. Description of the Related Art

U.S. Pat. No. 8,319,177 and U.S. Pat. No. 7,227,134 disclose a field asymmetric ion mobility spectrometer. The field asymmetric ion mobility spectrometer is used to separate at least one kind of material selectively from a mixture containing two or more kinds of materials. The at least one kind of separated material is detected with a detector included in the field asymmetric ion mobility spectrometer.

SUMMARY

The present invention provides a field asymmetric ion mobility spectrometer for selectively separating at least one kind of material from a mixture containing two or more kinds of materials, comprising:

an ionizer for ionizing the two or more kinds of materials contained in the mixture; and a filter for selecting the at least one kind of material from the two or more kinds of the ionized materials, wherein the filter is adjacent to the ionizer;

the filter comprises a first electrode group and a second electrode group;

the filter comprises a first plate-like electrode, a second plate-like electrode, a third plate-like electrode, and a fourth plate-like electrode, the first electrode group includes the first plate-like electrode and the third plate-like electrode;

the second electrode group includes the second plate-like electrode and the fourth plate-like electrode;

each of the first to fourth plate-like electrodes has a principal plane parallel to a direction from the ionizer toward the filter;

the second plate-like electrode is located between the first plate-like electrode and the third plate-like electrode;

the third plate-like electrode is located between the second plate-like electrode and the fourth plate-like electrode;

the third plate-like electrode is electrically connected to the first plate-like electrode;

the fourth plate-like electrode is electrically connected to the second plate-like electrode;

a first interspace is formed between the first plate-like electrode and the second plate-like electrode;

a second interspace is formed between the second plate-like electrode and the third plate-like electrode;

a third interspace is formed between the third plate-like electrode and the fourth plate-like electrode; and the first electrode group is electrically insulated from the second electrode group.

The present invention also includes a method for selectively separating at least one kind of material from a mixture containing two or more materials using the present field asymmetric ion mobility spectrometer.

The present invention provides a field asymmetric ion mobility spectrometer having high separation ability.

DETAILED DESCRIPTION OF THE EMBODIMENT

Hereinafter, the embodiment of the present invention will be described with reference to the drawings.

First, a field asymmetric ion mobility spectrometer (hereinafter, referred to as "FAIMS") will be described.

The field asymmetric ion mobility spectrometer is used to selectively separate at least one kind of material from a mixture containing two or more kinds of materials.

Figure 1:
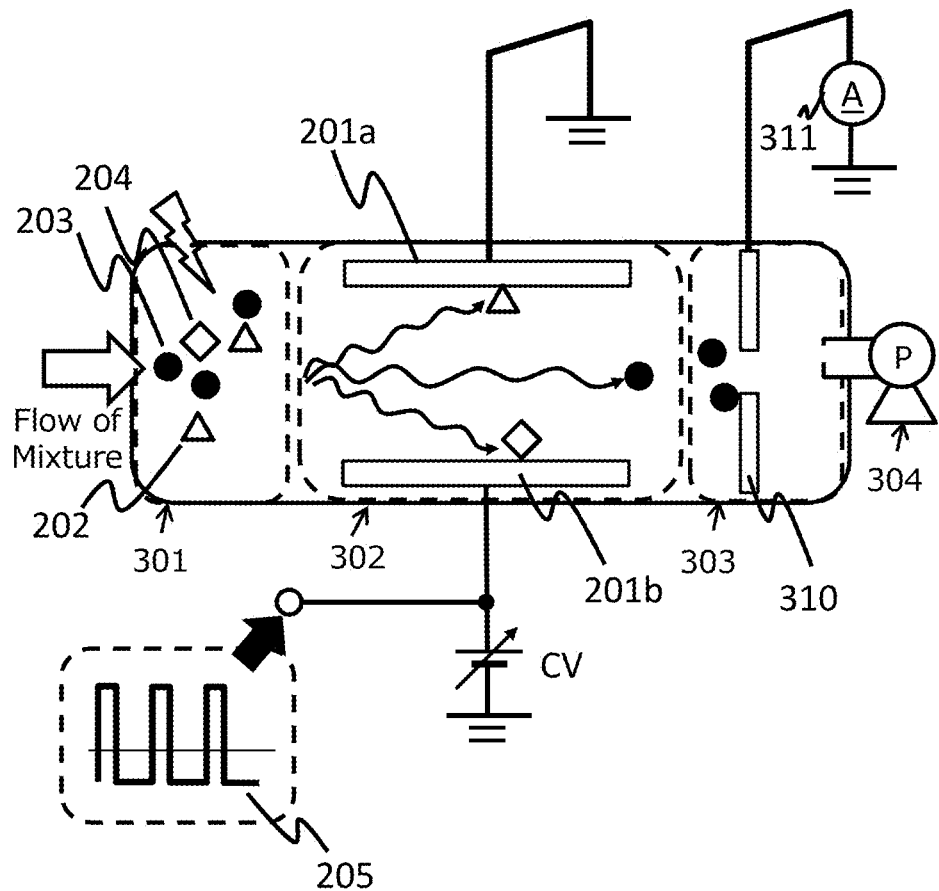
FIG. 1 shows a schematic view of a field asymmetric ion mobility spectrometer.

FIG. 1 shows a schematic view of the field asymmetric ion mobility spectrometer. As shown in FIG. 1, the field asymmetric ion mobility spectrometer comprises an ionizer 301 and a filter 302. Two or more kinds of materials contained in the mixture are ionized with the ionizer 301. At least one kind of material is selected from the two or more kinds of ionized materials through the filter 302.

(Ionizer 301)

The mixture to be supplied to the ionizer 301 is a liquid or a gas. The present inventors assume in the present specification that the mixture contains three kinds of gases 202-204. The gases 202-204 are ionized with the ionizer 301.

For more detail of the ionizer 301, see U.S. Pat. No. 8,319,177 and U.S. Pat. No. 7,227,134. These patents are incorporated herein by reference.

(Filter 302)

Then, the ionized gases 202-204 are supplied to the filter 302 located adjacent to the ionizer 301.

The filter 302 comprises a first plate-like electrode 201a and a second plate-like electrode 201b which are disposed parallel to each other. The first electrode 201a is grounded. On the other hand, the second electrode 201b is connected to a power supply 205. The power supply 205 is used to apply an asymmetric alternating voltage to the second electrode 201b. A compensation voltage CV may be superposed on the asymmetric alternating voltage. The asymmetric alternating voltage applied to the second electrode 201b will be described later.

The three kinds of ionized gases 202-204 are supplied between the grounded first electrode 201a and the second electrode 201b to which the asymmetric alternating voltage is applied. The three kinds of gases 202-204 are influenced by an electric field generated between the first electrode 201a and the second electrode 201b.

Figure 2:
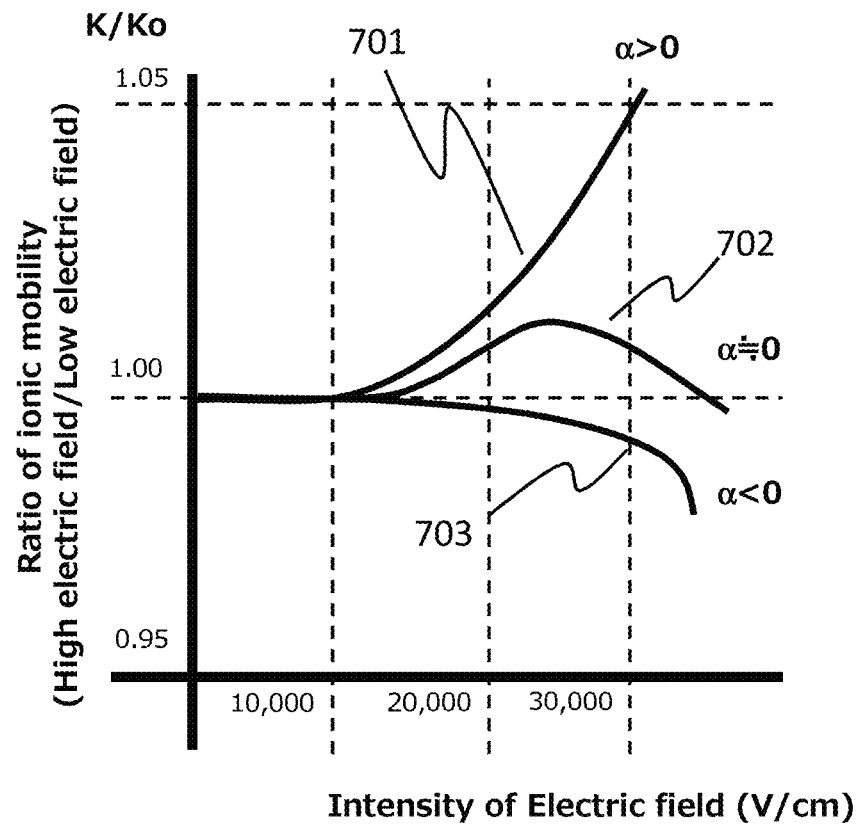
FIG. 2 is a graph indicating a relation between an intensity of an electric field and a ratio of ionic mobility.

FIG. 2 is a graph indicating a relation between an intensity of the electric field and a ratio of ionic mobility. As indicated by the referential sign 701 included in FIG. 2, some of ionized gases migrate more actively with an increase in the electric field intensity. Ions having a mass-to-charge ratio of less than 300 exhibit such a migration.

As indicated by the referential sign 702 included in FIG. 2, some of ionized gases migrate more actively with an increase in the electric field intensity; however, they migrate less actively with a further increase in the electric field intensity.

As indicated by the referential sign 703 included in FIG. 2, some of ionized gases migrate less actively with an increase in the electric field intensity. Ions having a mass-to-charge ratio of not less than 300 exhibit such a migration.

Due to such difference of properties, as shown in FIG. 1, the three kinds of gases 202-204 go in different directions in the filter 302. Only the gas 203 is discharged out of the filter 302, whereas the gas 202 is trapped on the surface of the first electrode 201a, and the gas 204 is trapped on the surface of the second electrode 201b. In this way, only the gas 203 is selectively separated from the three kinds of gases. In other words, only the gas 203 is discharged out of the filter 302.

The intensity of the electric field is appropriately set depending on the nature of the ions to be separated.

Next, the characteristics of the field asymmetric ion mobility spectrometer according to the present embodiment will be described below.

The field asymmetric ion mobility spectrometer according to the present embodiment is characterized by the structure of the filter 302.

Figure 3:
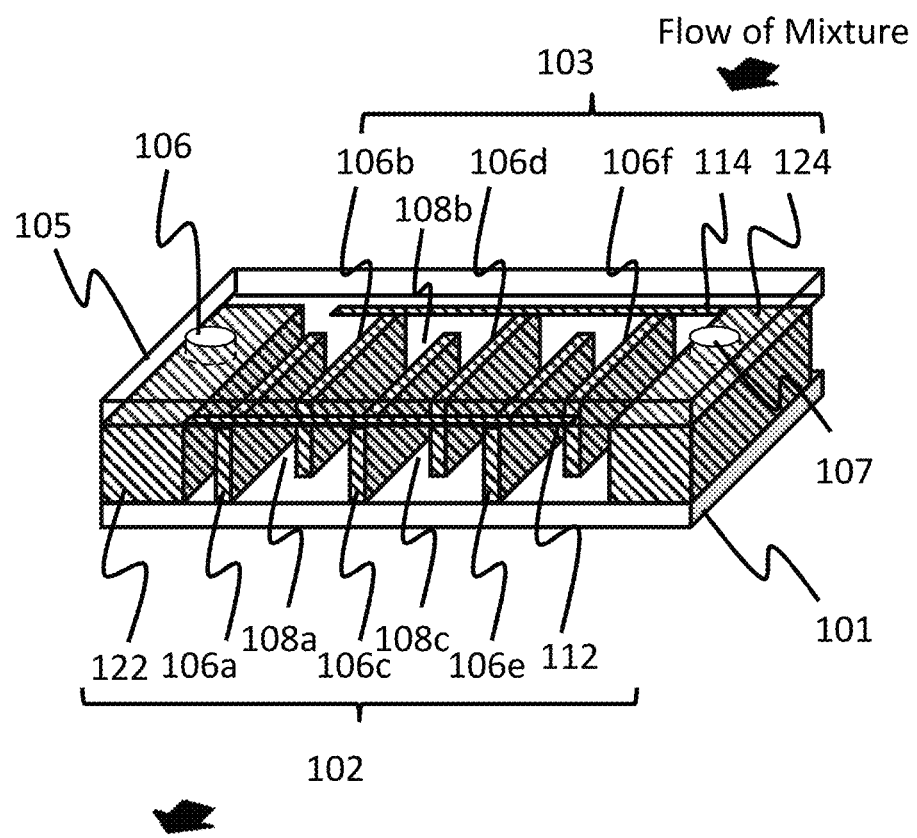
FIG. 3 shows a schematic view of a filter according to an embodiment.

FIG. 3 shows a schematic view of the filter 302 according to the present embodiment. As shown in FIG. 3, the filter 302 comprises a first electrode group 102 and a second electrode group 103. Needless to say, the filter 302 according to the present embodiment is included in the field asymmetric ion mobility spectrometer.

The filter 302 comprises a first plate-like electrode 106a, a second plate-like electrode 106b, a third plate-like electrode 106c and a fourth plate-like electrode 106d.

The first electrode group 102 includes the first plate-like electrode 106a and the third plate-like electrode 106c. The second electrode group 103 includes the second plate-like electrode 106b and the fourth plate-like electrode 106d. In the inside of the filter 302, the first electrode group 102 is electrically insulated from the second electrode group 103.

Each of the first to fourth plate-like electrodes 106a-106d has a principal plane parallel to the direction from the ionizer 301 toward the filter 302 (i.e., the flow direction of the mixture). The black arrow included in FIG. 3 shows the flow direction of the mixture (i.e., the direction from the ionizer 301 toward the filter 302).

As shown in FIG. 3, the second plate-like electrode 106b is located between the first plate-like electrode 106a and the third plate-like electrode 106c. The third plate-like electrode 106c is located between the second plate-like electrode 106b and the fourth plate-like electrode 106d.

The filter 302 shown in FIG. 1 further comprises a fifth plate-like electrode 106e and a sixth plate-like electrode 106f. The fifth plate-like electrode 106e is included in the first electrode group 102. The sixth plate-like electrode 106f is included in the second electrode group 103.

The filter 302 may comprise more plate-like electrodes 106. The $n^{th}$ plate-like electrode 106 is located between the $(n-1)^{th}$ plate-like electrode 106 and the $(n+1)^{th}$ plate-like electrode 106 (n represents a natural number of not less than 2). The $n^{th}$ plate-like electrode 106 has a principal plane parallel to the direction from the ionizer 301 toward the filter 302 (i.e., the flow direction of the mixture). The first electrode group 102 includes the $(2m-1)^{th}$ plate-like electrodes 106 (m represents an integer of not less than 1). The second electrode group 103 includes the $2m^{th}$ plate-like electrodes 106.

An interspace 108 is formed between adjacent two plate-like electrodes 106. Specifically, a first interspace 108a is formed between the first plate-like electrode 106a and the second plate-like electrode 106b. Similarly, a second interspace 108b is formed between the second plate-like electrode 106b and the third plate-like electrode 106c. A third interspace 108c is formed between the third plate-like electrode 106c and the fourth plate-like electrode 106d.

Hereinafter, a process for selectively separating the at least one kind of material from the mixture containing the two or more materials in the inside of the filter 302 according to the present embodiment will be described. Hereinafter, the present inventors assume that the mixture contains the two kinds of gases 202-203.

The gases 202-203 ionized with the ionizer 301 are supplied to the filter 302. The second electrode group 103 is grounded, whereas an asymmetric alternating voltage is applied from the power supply 205 to the first electrode group 102.

Figure 4A:
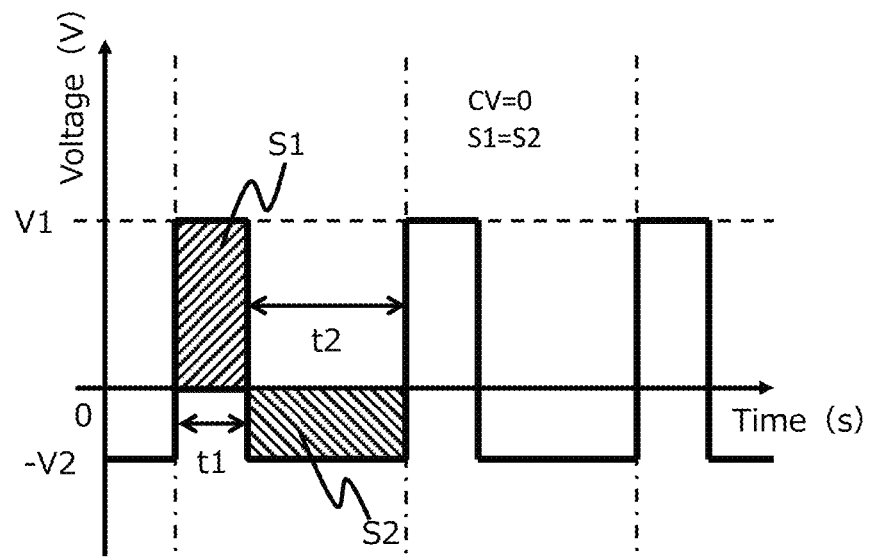
FIG. 4A is a graph indicating a relation between time and an asymmetric alternating voltage applied to a first electrode group.

FIG. 4A is a graph indicating a relation between time and the asymmetric alternating voltage applied to the first electrode group 102. In FIG. 4A, the compensation voltage is 0 volts. A positive voltage V1 (>0) is applied to the first electrode group 102 during a period t1. A negative voltage V2 (<0) is applied to the first electrode group 102 during a period t2. This is repeated. An area S1 defined by a product of V1·t1 is equal to an area S2 defined by a product of |V2|·t2.

Desirably, the period t1 is not less than 6 nanoseconds and not more than 100 nanoseconds. Desirably, the positive voltage V1 is not less than 67.5 volts and not more than 118.125 volts and the negative voltage V2 is not less than 16 volts and not more than 28.4 volts. Generally, the absolute value of the positive voltage V1 is greater than the absolute value of the negative voltage V2. However, as shown in FIG. 4C and FIG. 4D, the absolute value of the positive voltage V1 may be smaller than the absolute value of the negative voltage V2. Desirably, the asymmetric alternating voltage has a frequency of not less than 2 MHz and not more than 30 MHz.

The asymmetric alternating voltage shown in FIG. 4A is a square wave. However, in place of the square wave, the asymmetric alternating voltage may be a sine wave.

Figure 4B:
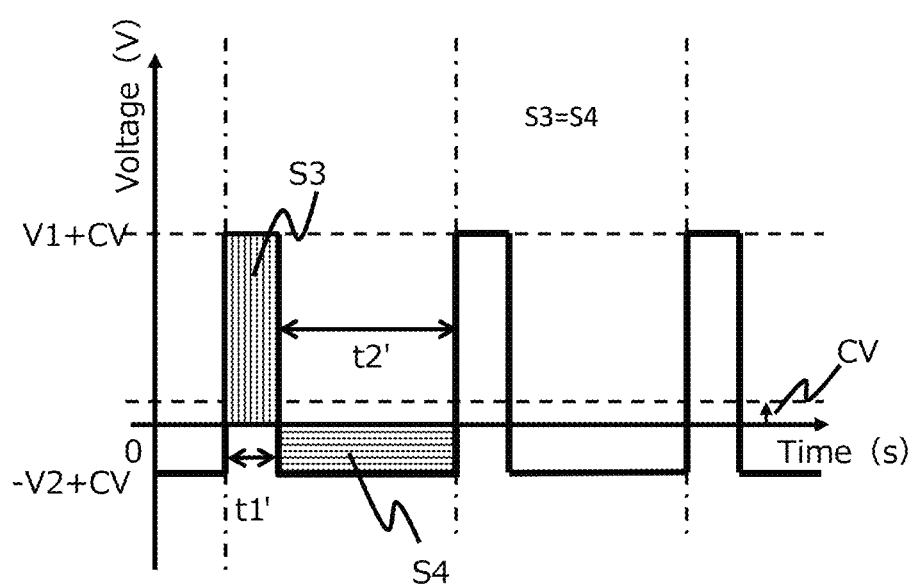
FIG. 4B is a graph indicating a relation between time and the asymmetric alternating voltage applied to the first electrode group.
Figure 4C:
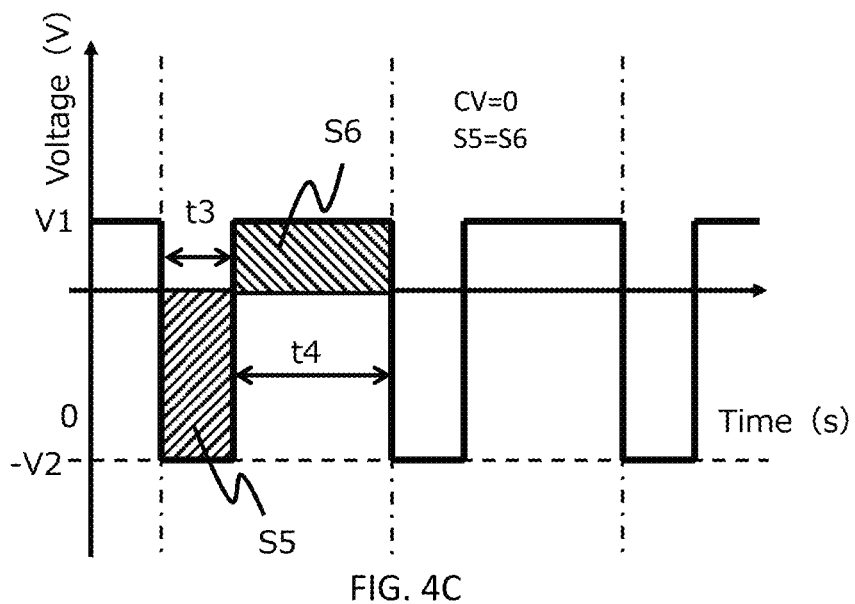
FIG. 4C is a graph indicating a relation between time and the asymmetric alternating voltage applied to the first electrode group.
Figure 4D:
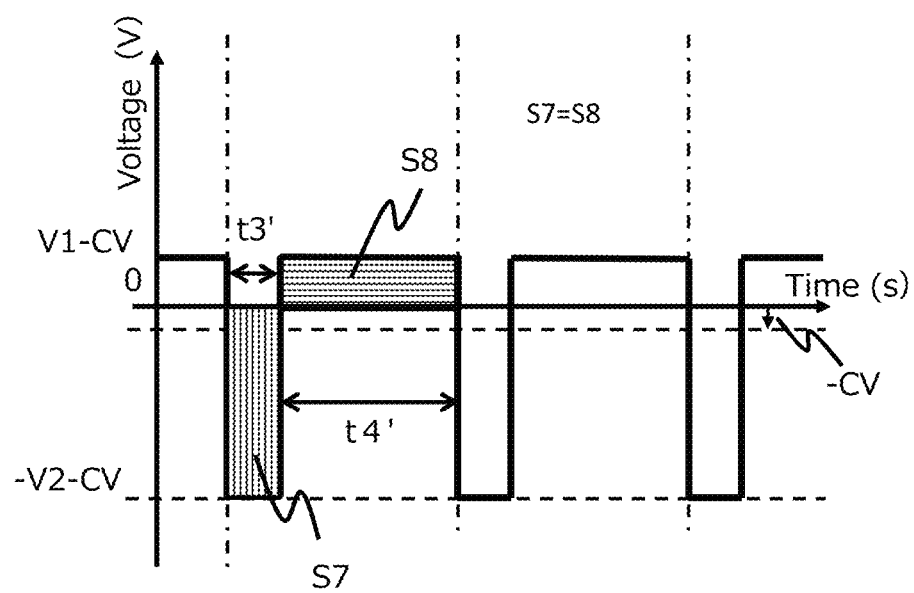
FIG. 4D is a graph indicating a relation between time and the asymmetric alternating voltage applied to the first electrode group.

FIG. 4B is also a graph indicating a relation between time and the asymmetric alternating voltage applied to the first electrode group 102. In FIG. 4B, the compensation voltage CV is superposed on the asymmetric alternating voltage. While the frequency is maintained constant, the duty ratio of the asymmetric alternating voltage is adjusted in such a manner that an area S3 defined by a product of (V1+CV)·t1' is equal to an area S4 defined by a product of |−V2+CV|·t2'. Desirably, the compensation voltage CV is not less than −20 volts and not more than 20 volts.

Figure 5:
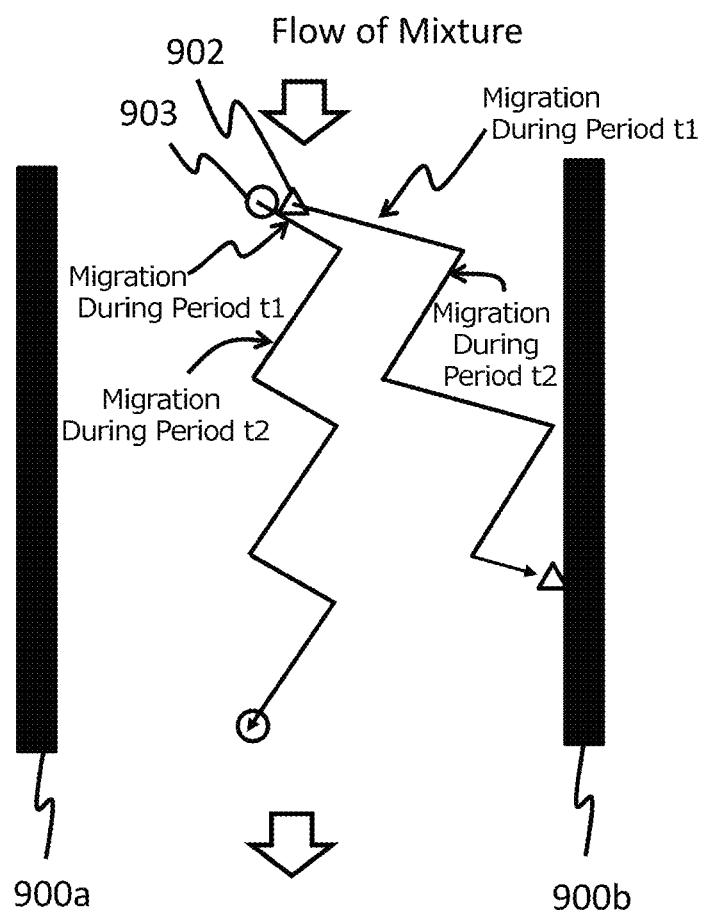
FIG. 5 shows a schematic top view of migration of two kinds of ionized gases between a pair of plate-like electrodes included in a conventional filter.

FIG. 5 shows a schematic top view of migration of two kinds of ionized gases 902-903 between a pair of plate-like electrodes 900a and 900b included in a conventional filter. The plate-like electrode 900a is grounded and the plate-like electrode 900b is electrically connected to the power supply 205. The arrow included in FIG. 5 indicates the flow direction of the mixture (i.e., the direction from the ionizer 301 toward the filter 302).

As shown in FIG. 5, during the period t1, the ionized gases 902 and 903 are drawn toward the plate-like electrode 900b. On the other hand, during the period t2, the ionized gas 902 and 903 are drawn toward the plate-like electrode 900a. With regard to the gas 903, the horizontal migration distance during the period t1 is substantially equal to the horizontal migration distance during the period t2. On the other hand, with regard to the gas 902, the horizontal migration distance during the period t1 is greater than the horizontal migration distance during the period t2. Therefore, the gas 903 goes along the pair of plate-like electrodes 900a and 900b, whereas the gas 903 is trapped on the surface of the plate-like electrode 900b.

However, in case where the electric field applied to the gas 902 during the period t1 is too small, in case where the length of the electrode 900 is too short, or in case where the interspace between the electrodes 900a and 900b is too large, the gas 902 fails to be trapped on the surface of the plate-like electrode 900b. In other words, the gas 902 is discharged together with the gas 903 out of the filter. Consequently, the gas 902 fails to be separated from the mixture containing the gas 902 and the gas 903. As just described, the conventional filter shown in FIG. 5 has low separation ability.

Figure 6:
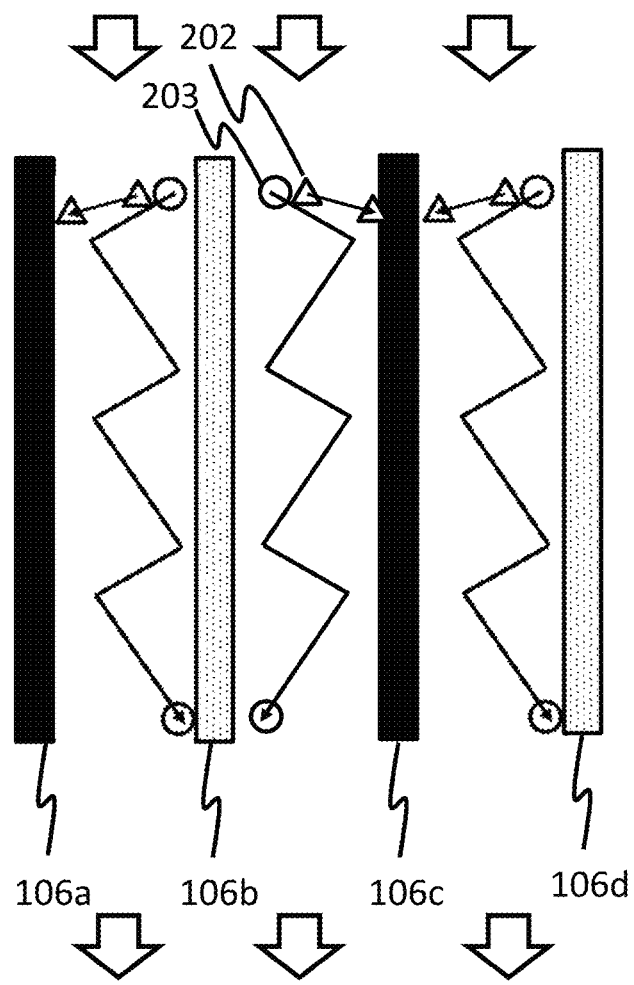
FIG. 6 shows a schematic top view of migration of two kinds of ionized gases between first to fourth plate-like electrodes included in a filter according to the embodiment.

On the other hand, FIG. 6 shows a schematic top view of the migration of the two kinds of ionized gases 202-203 between the first to fourth plate-like electrodes 106a-106d included in the filter 302 according to the present embodiment. As mentioned above, the first plate-like electrode 106a and the third plate-like electrode 106c are electrically connected to the power supply 205. On the other hand, the second plate-like electrode 106b and the fourth plate-like electrode 106d are grounded.

During the period t1, the ionized gases 202 and 203 are drawn toward one of the plate-like electrodes included in the first electrode group 102 (i.e., the first plate-like electrode 106a or the third plate-like electrode 106c). On the other hand, during the period t2, the ionized gases 202 and 203 are drawn toward one of the plate-like electrodes included in the second electrode group 103 (i.e., the second plate-like electrode 106b or the fourth plate-like electrode 106d).

With regard to the gas 203, the horizontal migration distance during the period t1 is substantially equal to the horizontal migration distance during the period t2. On the other hand, with regard to the gas 202, the horizontal migration distance during the period t1 is greater than the horizontal migration distance during the period t2.

As is clear from the comparison of FIG. 6 to FIG. 5, even if the electric field applied to the gas 202 during the period t1 is small or even if the plate-like electrodes 106 are short, the ionized gas 202 is trapped on the surfaces of the plate-like electrodes 106, whereas the ionized gas 203 goes through the filter 302 along the plate-like electrodes 106 and is discharged out of the filter 302. In this way, using the filter 302 according to the present embodiment, the objective at least one kind of ions (i.e., the ionized gas 203) are efficiently separated from the mixture containing the two or more kinds of ions. As just described, the filter shown in FIG. 6 according to the present embodiment has high separation ability.

The electric field applied to the gas is adjusted depending on the nature of the objective ionized gas (i.e., the ionized gas 203). As one example, during the period t1, an electric field of not less than 20,000 volts/cm and not more than 70,000 volts/cm may be applied to the gas. During the period t2, an electric field of not less than 1,000 volts/cm and not more than 10,000 volts/cm may be applied. In the filter 302 according to the present embodiment, the interspace 801 between the adjacent two plate-like electrodes 106 may be not less than 10 micrometers and not more than 35 micrometers. The plate-like electrode 106 may have a length of not less than 300 micrometers and not more than 10,000 micrometers.

The filter 302 according to the present embodiment will be described more specifically.

As shown in FIG. 3, the filter 302 has a shape of a rectangular parallelepiped. It is desirable that the filter 302 comprises a first insulative substrate 101 and a second insulative substrate 105 which are parallel to each other. The plate-like electrodes 106 are located between the first insulative substrate 101 and the second insulative substrate 105. Each of the plate-like electrodes 106 has a normal line perpendicular to the thickness direction of the first insulative substrate 101 (i.e., the vertical direction on the paper). Furthermore, each of the plate-like electrodes 106 has a principal plane parallel to the flow direction of the mixture (i.e., the direction from the ionizer 301 toward the filter 302).

As just described, the plate-like electrodes 106 are provided between the first insulative substrate 101 and the second insulative substrate 105 in such a manner that the plate-like electrodes 106 stand vertically on the first insulative substrate 101.

The backside of the second insulative substrate 105 is provided with a first belt-like electrode 112 and a second belt-like electrode 114. The first belt-like electrode 112 is included in the first electrode group 102 and electrically connected to the $(2m-1)^{th}$ plate-like electrodes 106 (e.g., the first plate-like electrode 106a, the third plate-like electrode 106c, and the fifth plate-like electrode 106e). The second belt-like electrode 114 is included in the second electrode group 103 and electrically connected to the $2m^{th}$ plate-like electrodes 106 (e.g., the second plate-like electrode 106b, the fourth plate-like electrode 106d and the sixth plate-like electrode 106f). As shown in FIG. 3, it is desirable that the first belt-like electrode 112 and the second belt-like electrode 114 are extended along the direction parallel to the normal line of the first plate-like electrode 106a (i.e., along the horizontal direction on the paper).

As just described, it is desirable that each of the first electrode group 102 and the second electrode group 103 has a shape of a comb. In the top view, the comb-shaped first electrode group 102 and the comb-shaped second electrode group 103 are engaged with each other.

It is desirable that the first electrode group 102 includes a first wall electrode 122 located at one end of the filter 302 (at the left end on the paper). Similarly, it is desirable that the second electrode group 103 includes a second wall electrode 124 located at the other end of the filter 302 (at the right end on the paper). Needless to say, a pair of openings are provided at the other two lateral surfaces of the filter 302 (i.e., at the front and back sides on the paper). The mixture enters the filter 302 through one of the openings which is at the back side on the paper. The at least one kind of objective material is discharged out of the filter 302 through the other opening which is at the front side on the paper.

The second insulative substrate 105 is provided with a first through-hole 161 and a second through-hole 162. The first wall electrode 122 is electrically connected to the power supply 205 through the first through-hole 161. Similarly, the second wall electrode 124 is grounded through the second through-hole 162.

Hereinafter, a fabrication method of the filter 302 according to the present embodiment will be described.

Figure 7A:
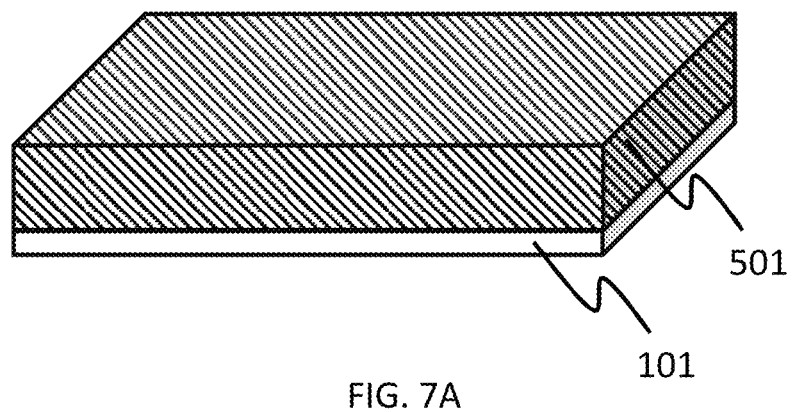
FIG. 7A shows a schematic view of one step included in a method for producing the filter according to the embodiment.
Figure 7B:
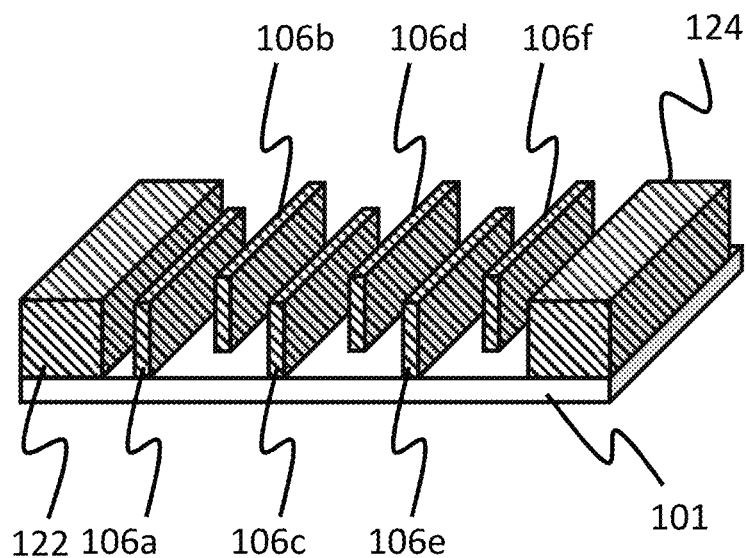
FIG. 7B shows a schematic view of one step, subsequent to FIG. 7A, included in the method for producing the filter according to the embodiment.

First, as shown in FIG. 7A, a silicon substrate 501 having a gold layer (not shown) on the surface thereof is stacked on the first insulative substrate 101, such as a glass substrate, having an aluminum layer (not shown) on the surface thereof in such a manner that the stacked structure of the glass layer/the aluminum layer/the silicon layer/the gold layer is formed. The silicon substrate 501 may have a thickness of not less than 300 micrometers and not more than 700 micrometers. The silicon substrate 501 is doped with impurities such as antimony. For this reason, the silicon substrate 501 is conductive. The gold layer may be formed by coating the first insulative substrate 101 with gold by a sputtering method or by a vapor deposition method. The gold layer may have a thickness of not less than 200 nanometers and not more than 300 nanometers. The aluminum layer may be formed by coating the silicon substrate doped with the impurities such as antimony with aluminum by a sputtering method or by a vapor deposition method. The aluminum layer may have a thickness of approximately 1 micrometer. The silicon substrate 501 having the aluminum layer on the surface thereof is joined onto the first insulative substrate 101 by an anode boding method.

Then, a photoresist is applied onto the gold layer exposed on the uppermost surface. The photoresist is exposed with a mask to form a resist pattern (not shown). Using the resist pattern as a mask, a part of the gold layer is removed by a wet-etching method. Furthermore, using the resist pattern as a mask, a part of the silicon layer is removed by a Bosch method. Using the resist pattern as a mask, a part of the aluminum layer is removed. In this way, the plate-like electrodes 106, the first wall electrode 122, and the second wall electrode 124 are formed on the first insulative substrate 101.

Figure 7C:
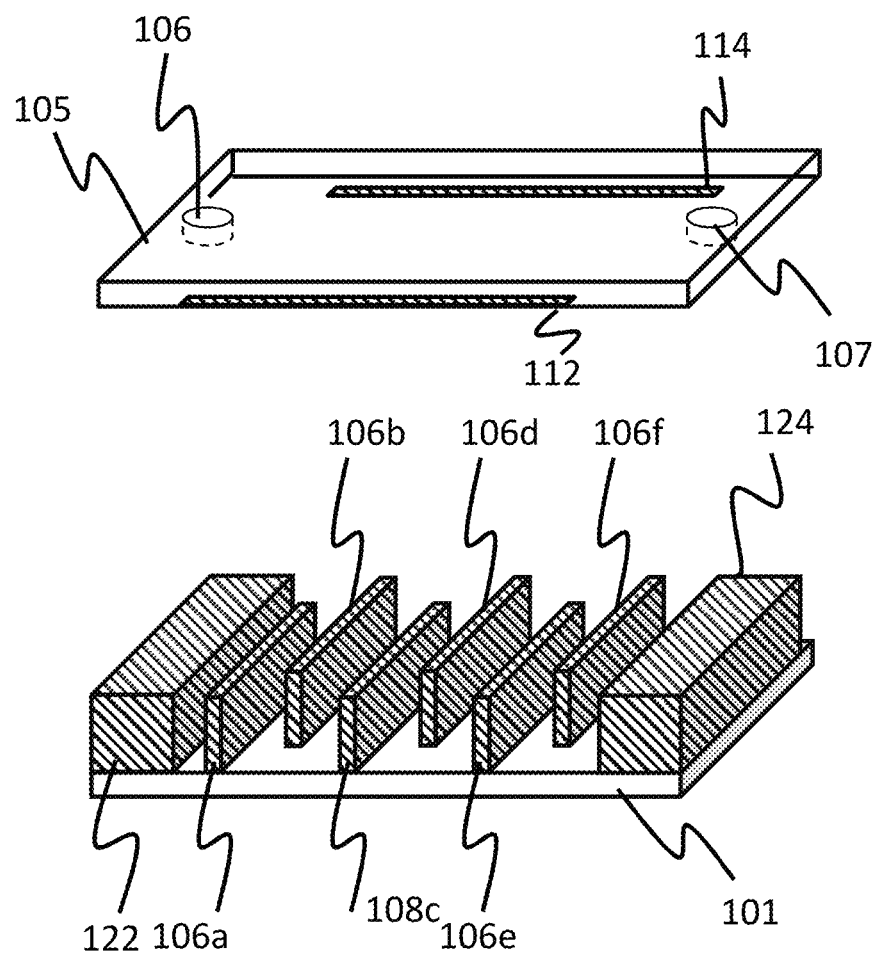
FIG. 7C shows a schematic view of one step, subsequent to FIG. 7B, included in the method for producing the filter according to the embodiment.

Finally, as shown in FIG. 7C, the second insulative substrate 105 having the first belt-like electrode 112 and the second belt-like electrode 114 on the back surface thereof is joined onto the first insulative substrate 101. Upon joining, the first belt-like electrode 112 is electrically connected to the $(2m-1)^{th}$ plate-like electrodes 106 (e.g., the first plate-like electrode 106a, the third plate-like electrode 106c and the fifth plate-like electrode 106e). Similarly, the second belt-like electrode 114 is electrically connected to the $2m^{th}$ plate-like electrodes 106 (e.g., the second plate-like electrode 106b, the fourth plate-like electrode 106d and the sixth plate-like electrode 106f). In this way, the filter 302 shown in FIG. 3 is obtained.

(Other Matters)
(Ion Detector)

As shown in FIG. 1, the field asymmetric ion mobility spectrometer may comprise an ion detector 303. The ion detector 303 is located adjacent to the filter 302. In other words, the filter 302 is located between the ionizer 301 and the ion detector 303.

A known ion detector 303 as disclosed in U.S. Pat. No. 8,319,177 and U.S. Pat. No. 7,227,134 may be used. The at least one kind of material which has travelled through the filter 302 (i.e., the gas 203) may be detected with the ion detector 303. The at least one kind of material which has reached the ion detector 303 (i.e., the gas 203) gives its electrical charge to an electrode 310 included in the ion detector 303. The value of the electric current which flows proportionally to the amount of the given electrical charge is measured with an ammeter 311. The gas 203 is identified on the basis of the value of the electric current measured with the ammeter 311.

(Pump or Electrostatic Field)

As shown in FIG. 1, the field asymmetric ion mobility spectrometer may comprise a pump 304. The mixture is sucked with the pump 304 from the ionizer 301 to the ion detector 303 through the filter 302.

In place of the pump 304, an electrostatic field may be used. In other words, the mixture may flow from the ionizer 301 to the ion detector 303 through the filter 302 using the electrostatic field. In this case, the field asymmetric ion mobility spectrometer comprises a pair of electrodes (not shown). The ionizer 301, the filter 302 and the ion detector 303 are sandwiched between the pair of electrodes. A direct voltage is applied to the pair of electrodes. The ionized mixture may flow from the ionizer 301 to the ion detector 303 through the filter 302 due to the direct current applied to the pair of electrodes.

INDUSTRIAL APPLICABILITY

The field asymmetric ion mobility spectrometer according to the present invention can be used to detect a component contained in a biogas released from a biological body or to detect a hazardous component contained in an environmental gas.

REFERENTIAL SIGNS LIST

101 First insulative substrate
102 First electrode group
103 Second electrode group
105 Second insulative substrate
106a First plate-like electrode
106b Second plate-like electrode
106c Third plate-like electrode
106d Fourth plate-like electrode
106e Fifth plate-like electrode
106f Sixth plate-like electrode
108a First interspace
108b Second interspace
108c Third interspace
112 First belt-like electrode
114 Second belt-like electrode
122 First wall electrode
124 Second wall electrode
161 First through hole 162 Second through hole
201a First plate-like electrode
201b Second plate-like electrode
202 Gas
203 Gas
204 Gas
205 Power supply
301 Ionizer
302 Filter
303 Ion detector
304 Pump
311 Ammeter
900a Plate-like electrode
900b Plate-like electrode
902 Gas
903 Gas

The invention claimed is:

1. A field asymmetric ion mobility spectrometer for selectively separating at least one kind of material from a mixture containing two or more kinds of materials, the field asymmetric ion mobility spectrometer comprising:
an ionizer for ionizing the two or more kinds of materials contained in the mixture; and
a filter for selecting the at least one kind of material from the two or more kinds of the ionized materials,
wherein
the filter is adjacent to the ionizer;
the filter comprises a first plate-like electrode, a second plate-like electrode, a third plate-like electrode, and a fourth plate-like electrode;
the first plate-like electrode and the third plate-like electrode are included in a first electrode group;
the second plate-like electrode and the fourth plate-like electrode are included in a second electrode group;
each of the first to fourth plate-like electrodes has a principal plane parallel to a direction from the ionizer toward the filter;
the second plate-like electrode is located between the first plate-like electrode and the third plate-like electrode;
the third plate-like electrode is located between the second plate-like electrode and the fourth plate-like electrode;
the third plate-like electrode is electrically connected to the first plate-like electrode;
the fourth plate-like electrode is electrically connected to the second plate-like electrode;
a first interspace is formed between the first plate-like electrode and the second plate-like electrode;
a second interspace is formed between the second plate-like electrode and the third plate-like electrode;
a third interspace is formed between the third plate-like electrode and the fourth plate-like electrode; and
the first electrode group is electrically insulated from the second electrode group.

2. The field asymmetric ion mobility spectrometer according to claim 1, wherein
the filter comprises a first insulative substrate and a second insulative substrate which are parallel to each other;
the first to fourth plate-like electrodes are located between the first insulative substrate and the second insulative substrate; and
each of the first to fourth plate-like electrodes has a normal line perpendicular to a thickness direction of the first insulative substrate.

3. The field asymmetric ion mobility spectrometer according to claim 2, wherein
the first electrode group comprises a first belt-like electrode;
the second electrode group comprises a second belt-like electrode;
the first belt-like electrode is provided on a back surface of the second insulative substrate;
the second belt-like electrode is provided on the back surface of the second insulative substrate;
the first belt-like electrode is electrically connected to the first plate-like electrode and the third plate-like electrode; and
the second belt-like electrode is electrically connected to the second plate-like electrode and the fourth plate-like electrode.

4. The field asymmetric ion mobility spectrometer according to claim 3, wherein
the first and second belt-like electrodes are extended to a direction parallel to the normal line of the first plate-like electrode.

5. The field asymmetric ion mobility spectrometer according to claim 1, further comprising:
a detector for detecting the at least one kind of material selected with the filter;
wherein
the filter is located between the ionizer and the detector.

6. The field asymmetric ion mobility spectrometer according to claim 1, wherein
each of the first interspace, the second interspace, and the third interspace has a width of not less than 10 micrometers and not more than 35 micrometers.

7. The field asymmetric ion mobility spectrometer according to claim 1, wherein
each of the first to fourth plate-like electrodes has a length of not less than 300 micrometers and not more than 10,000 micrometers.

8. A method for selectively separating at least one kind of material from a mixture containing two or more kinds of materials using a field asymmetric ion mobility spectrometer; the method comprising:
(a) preparing the field asymmetric ion mobility spectrometer comprising:
an ionizer for ionizing the two or more kinds of materials contained in the mixture; and
a filter for selecting the at least one kind of material from the two or more kinds of the ionized materials,
wherein
the filter is adjacent to the ionizer;
the filter comprises a first plate-like electrode, a second plate-like electrode, a third plate-like electrode, and a fourth plate-like electrode;
the first plate-like electrode and the third plate-like electrode are included in a first electrode group;
the second plate-like electrode and the fourth plate-like electrode are included in a second electrode group;
each of the first to fourth plate-like electrodes has a principal plane parallel to a direction from the ionizer toward the filter;
the second plate-like electrode is located between the first plate-like electrode and the third plate-like electrode;
the third plate-like electrode is located between the second plate-like electrode and the fourth plate-like electrode;
the third plate-like electrode is electrically connected to the first plate-like electrode;

the fourth plate-like electrode is electrically connected to the second plate-like electrode;
a first interspace is formed between the first plate-like electrode and the second plate-like electrode;
a second interspace is formed between the second plate-like electrode and the third plate-like electrode;
a third interspace is formed between the third plate-like electrode and the fourth plate-like electrode; and
the first electrode group is electrically insulated from the second electrode group;
(b) supplying the mixture containing the two or more kinds of materials to the ionizer to ionize the two or more kinds of materials contained in the mixture; and
(c) supplying the two or more kinds of the ionized materials to the filter to separate the at least one kind of material through the filter,
wherein
an asymmetric alternating voltage is applied between the first electrode group and the second electrode group; and
the at least one kind of the ionized material travels through the first-third interspaces, whereas other ionized materials are trapped on the principal planes of the first to fourth plate-like electrodes.

9. The method according to claim 8, wherein
the filter comprises a first insulative substrate and a second insulative substrate which are parallel to each other;
the first to fourth plate-like electrodes are located between the first insulative substrate and the second insulative substrate; and
each of the first to fourth plate-like electrodes has a normal line perpendicular to a thickness direction of the first insulative substrate.

10. The method according to claim 9, wherein
the first electrode group comprises a first belt-like electrode;
the second electrode group comprises a second belt-like electrode;
the first belt-like electrode is provided on a back surface of the second insulative substrate;
the second belt-like electrode is provided on the back surface of the second insulative substrate;
the first belt-like electrode is electrically connected to the first plate-like electrode and the third plate-like electrode; and
the second belt-like electrode is electrically connected to the second plate-like electrode and the fourth plate-like electrode.

11. The method according to claim 10, wherein
the first and second belt-like electrodes are extended to a direction parallel to the normal line of the first plate-like electrode.

12. The method according to claim 8, further comprising:
a detector for detecting the at least one kind of material selected with the filter;
wherein
the filter is located between the ionizer and the detector.

13. The method according to claim 8, wherein
each of the first interspace, the second interspace, and the third interspace has a width of not less than 10 micrometers and not more than 35 micrometers.

14. The method according to claim 8, wherein
each of the first plate-like electrode, the second plate-like electrode, the third plate-like electrode, and the fourth plate-like electrode has a length of not less than 300 micrometers and not more than 10,000 micrometers.

15. A filter used for a field asymmetric ion mobility spectrometer capable of selectively separating at least one kind of material from a mixture containing two or more kinds of materials, the filter comprising:
a first plate-like electrode;
a second plate-like electrode;
a third plate-like electrode; and
a fourth plate-like electrode, wherein
the first plate-like electrode and the third plate-like electrode are included in a first electrode group;
the second plate-like electrode and the fourth plate-like electrode are included in a second electrode group;
each of the first to fourth plate-like electrodes has a principal plane parallel to a direction from an ionizer towards a filter;
the second plate-like electrode is located between the first plate-like electrode and the third plate-like electrode;
the third plate-like electrode is located between the second plate-like electrode and the fourth plate-like electrode;
the third plate-like electrode is electrically connected to the first plate-like electrode;
the fourth plate-like electrode is electrically connected to the second plate-like electrode;
a first interspace is formed between the first plate-like electrode and the second plate-like electrode;
a second interspace is formed between the second plate-like electrode and the third plate-like electrode;
a third interspace is formed between the third plate-like electrode and the fourth plate-like electrode;
the first electrode group is electrically insulated from the second electrode group;
the filter comprises a first insulative substrate and a second insulative substrate which are parallel to each other;
the first to fourth plate-like electrodes are located between the first insulative substrate and the second insulative substrate;
each of the first to fourth plate-like electrodes has a normal line perpendicular to a thickness direction of the first insulative substrate;
the first electrode group comprises a first belt-like electrode;
the second electrode group comprises a second belt-like electrode;
the first belt-like electrode is provided on a back surface of the second insulative substrate;
the second belt-like electrode is provided on the back surface of the second insulative substrate;
the first belt-like electrode is electrically connected to the first plate-like electrode and the third plate-like electrode; and
the second belt-like electrode is electrically connected to the second plate-like electrode and the fourth plate-like electrode.

16. The filter according to claim 15, wherein
the first and second belt-like electrodes are extended to a direction parallel to the normal line of the first plate-like electrode.

17. The filter according to claim 15, wherein
each of the first interspace, the second interspace, and the third interspace has a width of not less than 10 micrometers and not more than 35 micrometers.

18. The filter according to claim 15, wherein
each of the first plate-like electrode, the second plate-like electrode, the third plate-like electrode, and the fourth plate-like electrode has a length of not less than 300 micrometers and not more than 10,000 micrometers.

* * * * *